(12) United States Patent
Oben

(10) Patent No.: US 7,718,200 B2
(45) Date of Patent: *May 18, 2010

(54) PLANT EXTRACT MIXTURES AND THEIR USES

(75) Inventor: Julius Enyong Oben, Yaounde (CM)

(73) Assignee: Gateway Health Alliances, Inc., Fairfield, CA (US)

( * ) Notice: Subject to any disclaimer, the term of this patent is extended or adjusted under 35 U.S.C. 154(b) by 117 days.

This patent is subject to a terminal disclaimer.

(21) Appl. No.: 11/464,474

(22) Filed: Aug. 14, 2006

(65) Prior Publication Data

US 2007/0202204 A1 Aug. 30, 2007

Related U.S. Application Data

(63) Continuation of application No. 10/069,743, filed as application No. PCT/GB00/03324 on Aug. 29, 2000, now Pat. No. 7,175,859.

(30) Foreign Application Priority Data

Aug. 27, 1999 (GB) .................................. 9920393.7

(51) Int. Cl.
*A01N 65/00* (2009.01)
(52) U.S. Cl. ..................................................... 424/725
(58) Field of Classification Search ...................... None
See application file for complete search history.

(56) References Cited

OTHER PUBLICATIONS

Onyechi, UA et al. British Journal of Nutrition (Nov. 1998); 80(5): 419-28. African plant foods rich in non-starch polysaccharides reduce postprandial blood glucose and insulin concentrations in health human subjects.*
Bell, S et al. Proceedings of the Nutrition Society *1993); 52(3): 372a. An investigation of the effects of two indigenous African foods, *Detarium microcarpum* and *Cissus rotundifolia* on rat plasma cholesterol levels.*
Obatomi, D K et al. Phytotherapy (1997); 11: 171-173. Metabolic and renal changes following the ingestion of African mistletoe extract in rats.*
Eriyamremu, G. E. et al., Clinica Dietologica (1995); 22(3-4): 101-110. Wholly compounded Nigerian diets alter rissue lipid profile in rats.*
Achola, K. J. et al. International Journal of Pharmacognosy (1996) ; Pharmacological acitivies of *Vernonia glabra*.*
Subbu, V. S., et al. Ind. J. Pharmac (1970) ; 2(3) : 91-97. Pharmacological and toxicological evaluation of an active principle obtained for the plant *Vitis quadrangularis*.*
Jainu, Mallika, et al. "Gastroprotective effect of *Cissus quadrangularis* extract in rats with experimentally induced ulcer."

*Indian J Med Res* 123, Jun. 2006, pp. 799-806, Department of Biochemistry, University of Madras, Chennai, India.
Jainu, M., et al. "Gastroprotective action of *Cissus quadrangularis* extract against NSAID induced gastric ulcer: role of proinflammatory cytokines and oxidative damage." *Chemico-Biological Interactions*, Jul. 10, 2006;161(3):262-70. Epub May 1, 2006.
Jo, Moody, et al. "Anti-sickling potential of a Nigerian herbal formula (ajawaron HF) and the major plant component (*Cissus populnea* L. CPK)." *Phytother Res.*, Dec. 2003; 17(10):1173-6.
Phondke, G.P., ed. *The Wealth of India: A Dictionary of Indian Raw Materials & Industrial Products*. "Raw Materials, vol. 3: Ca-Ci (Revised)." 1992, pp. 593-594. Publications & Information Directorate, Council of Scientific & Industrial Research, New Delhi.
Sen, S.P. "Study of the Active Constituents (Ketosteroids) of *Cissus quadrangularis*, Wall." *The Indian Journal of Pharmacy*, Sep. 1964, p. 247.
Mehta, Manisha. "Determination of Marker Constituents from *Cissus quadrangularis* Linn. and their Quantitation by HPTLC and HPTLC." *Phytochemical Analysis*, 2001:12, pp. 91-95. John Wiley & Sons, Ltd.
Subbu, V.S. Venkata. "Pharmacological and Toxicological Evaluation of an Active Principle Obtained from the Plant *Vitis quadrangularis*." *Ind.J. Pharmac.* (1970), 2 (3), pp. 91-97.
Prasad, G.C., et al. "Pathways and Site of Action of a Phytogenic Steroid from *Cissus quadrangularis*." *Jour. Res. Med.* (1972), 7:4, pp. 29-35.
Singh, S.P., et al. "An Experimental Study of Analgesic Activity of *Cissus quadrangularis*." *Indian Journal of Pharmacology*, (7984), pp. 162-163, (1984).
Prasad, G.C., et al. "Effect of *Cissus quadrangularis* on the Healing of Cortisone Treated Fractures." *Indian Journal of Medicine*, Jul. 1963, 51(4), pp. 667-676.
Udupa, K.N., et al. "The Effect of Phytogenic Anabolic Steroids in the Acceleration of Fracture Repair." *Life Sciences*, 1965, vol. 4, pp. 317-327. Pergamon Press, Ltd., Great Britain.
Chopra, S.S., et al. "Studies on *Cissus quadrangularis* in Experimental Fracture Repair: A Histopathological Study." *Indian J. Med. Res.*, Sep. 1976, 64:9, pp. 1365-1368.
Deka, D.K., et al. "Effect of *Cissus quadrangularis* in Accelerating Healing Process of Experimentally Fractured Radius-Ulna of Dog: A Preliminary Study." *Indian Journal of Pharmacology*, 1994; 26, pp. 44-45.

* cited by examiner

*Primary Examiner*—Michele Flood
(74) *Attorney, Agent, or Firm*—Steve P. Hassid

(57) ABSTRACT

A composition comprising extract of one or more plants of one or more of the following plant families: *Cissus*, *Vernonia* and *Brillantasia*. Such compositions have beneficial activity principally in controlling light gain and obesity, especially in conjunction with chitosan or a chitosan derivative and an antioxidant such as vitamin C.

6 Claims, 1 Drawing Sheet

Figure 1:
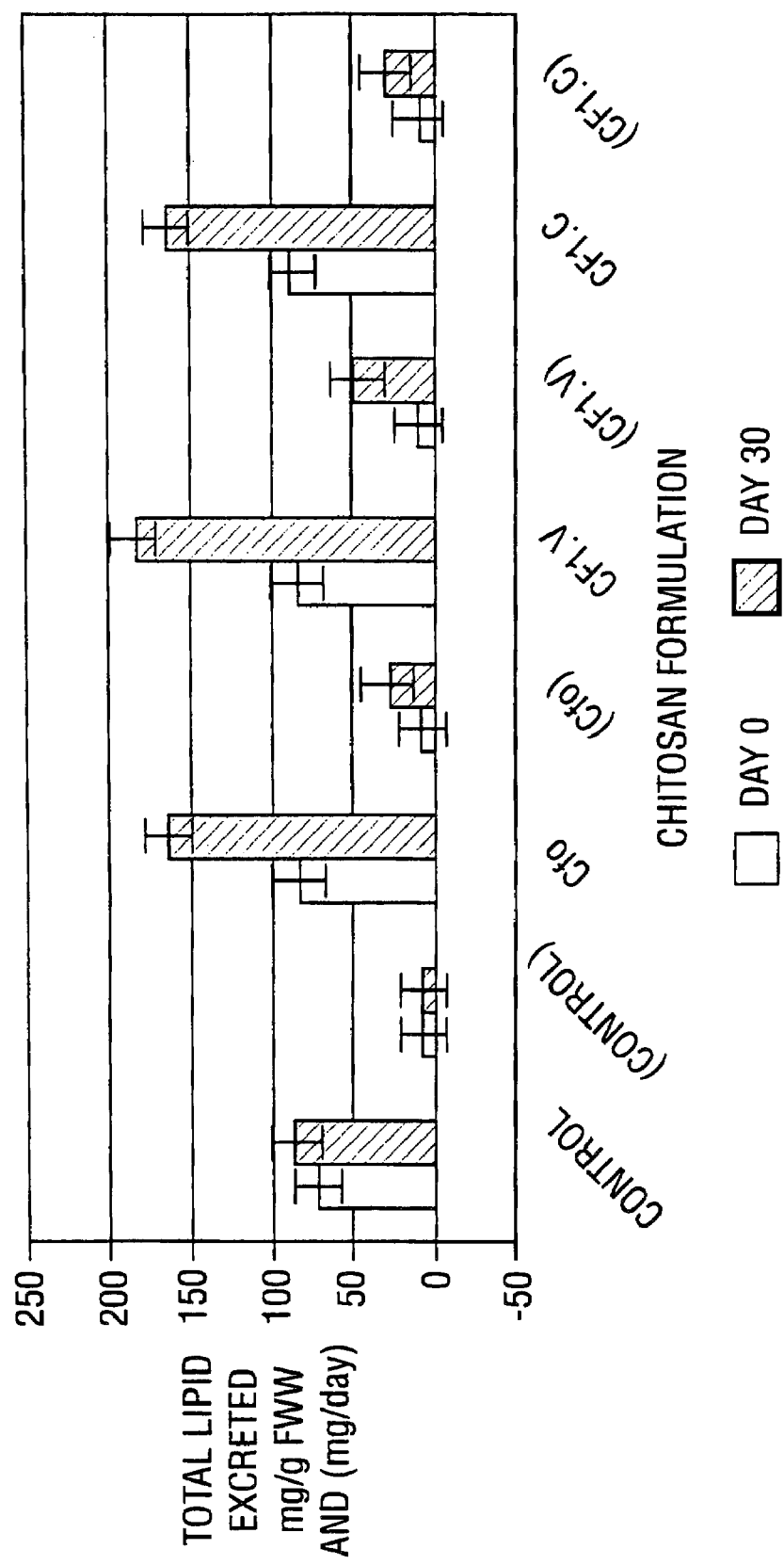

The effect of chitosan formulation on total fecal lipid excretion

PLANT EXTRACT MIXTURES AND THEIR USES

RELATED APPLICATIONS

This application is a continuation application of U.S. patent application Ser. No. 10/069,743, filed on Sep. 10, 2002, now U.S. Pat. No. 7,175,859 which claims the benefit of U.S. National Stage application number PCT/GB00/03324 under 35 U.S.C. §371, filed on Aug. 29, 2000, which claims benefit under 35 U.S.C. §119(a) to Great Britain Application No. 9920393.7, filed on Aug. 27, 1999. These applications are incorporated herein by reference.

BACKGROUND

The present disclosure is directed to the use of plant extracts from one or more plants of the *Cissus, Vernonia* and *Brillantasia* plant families to provide a variety of health related benefits, including but not limited to, enhancing fat-binding capacity, inhibiting carbohydrate breakdown, inhibiting amylase activity and/or improving nutrient absorption in the presence or absence of fat binding materials.

The present disclosure is also directed to the use of mixtures comprising plant extracts from plants in at least one of three families (one or more of *Cissus, Vernonia* and *Brillantasia*) to enhance fat-binding capacity as well as the inhibition of carbohydrate breakdown, amylase activity and nutrient absorption in the presence of fat binding materials. In at least on embodiment the mixtures can be combined with chitosan or chitosan derivatives to synergize their fat binding properties.

Fat binding materials e.g. chitosan have applications in industry and in health. In both cases, the binding capacity of these materials is limited because of their bulk. The new combination of plant extracts has the ability to enhance the fat binding capacity of such materials as well as alter the metabolism of other compounds in animals, including humans.

Chitosan is widely used for the control of weight. Its use is based on its ability to bind fatty acids in vitro and in vivo, thereby reducing the ability of the body to absorb and utilize dietary fats. By combining chitosan with two plant extracts; *Cissus quadrangularis* and *Vernonia glabra*, its ability to bind fatty acids and triacylglycerols in vitro was significantly increased ($p<0.05$ and $p<0.01$ respectively). This is reflected in the significantly higher fat content of the feces of subjects on chitosan or chitosan based formulations. Compared to chitosan, the combination of chitosan and *Cissus quadrangularis* significantly increased the fecal pH ($p<0.01$), fecal ash ($p<0.02$) and mineral content ($p<0.02$) in overweight women (BMI 25-29 kg/m$^2$) over a six month period, while decreasing the fecal water content ($p<0.01$). The combination of chitosan and *Vernonia glabra* did not alter the mineral content or the pH of the feces although it caused a significant increase ($p<0.05$) in fecal bulk. The results indicate that the chitosan and *Vernonia glabra* combination can be effectively used in long term weight control regimes.

Chitosan is a polysaccharide produced from chitin found in the exoskeletons of arthropods (crustaceans and insects) and the endoskeletons of cephalopods. It is widely spread in the biomass, being the most abundant biopolymer after cellulose. It is generally accepted that chitin is extensively acetylated while chitosan is largely deacetylated. Chitosan is a cationic glucosamine polymer with a high anion-exchange capacity as a result of quaternary ammonium ions. It is known to have a marked hypocholesterolemic effect in rats, alters bile acid metabolism and increases the HDL to total cholesterol ratio in broiler chickens. The hypocholesterolemic effect of chitosan can be theoretically explained by its ability to decrease lipid absorption and increase fecal cholesterol excretion. The alteration of bile acid can be due to the modification of colon pH.

Chitosan is widely used in weight control products. Its application is a result of its ability to bind triglycerides in vitro. In principle therefore, chitosan limits the amount of fat energy that can be absorbed and used by the body. The use of chitosan therefore does not find application only as a weight loss supplement, but also as a means of reducing blood lipids.

SUMMARY

The present disclosure is directed to the use of plant extracts from one or more plants of the *Cissus, Vernonia* and *Brillantasia* plant families to provide a variety of health related benefits, including but not limited to, enhancing fat-binding capacity, inhibiting carbohydrate breakdown, inhibiting amylase activity and/or improving nutrient absorption in the presence or absence of fat binding materials.

The present disclosure is also directed to the use of mixtures comprising plant extracts from plants in at least one of three families (one or more of *Cissus, Vernonia* and *Brillantasia*) to enhance fat-binding capacity as well as the inhibition of carbohydrate breakdown, amylase activity and/or nutrient absorption in the presence of fat binding materials. In at least on embodiment of the present disclosure, the mixtures can be combined with chitosan or chitosan derivatives to synergize their fat binding properties.

DRAWINGS

The above-mentioned features and objects of the present disclosure will become more apparent with reference to the following description taken in conjunction with the accompanying drawing.

FIG. 1 is a bar graph displaying the results of experiments measuring the effect thirty days of supplementation with an exemplary chitosan formulation had on total fecal lipid excretion.

DETAILED DESCRIPTION

We have investigated the effect of chitosan and chitosan based formulations on overweight women. Their BMI and body composition had been evaluated. The fecal weight, fecal pH, water content, calcium and magnesium content and total nitrogen were measured. The total blood lipid content and beneficial effects of plant supplements (extracts of *Vernonia glabra* and *Cissus quadrangularis*) on improved chitosan lipid binding has unexpectedly been found.

According to one aspect of the present invention there is provided a composition comprising extract of one or more plants of one or more of the following plant families: *Cissus, Vernonia* and *Brillantasia*. According to another aspect the invention provides uses of such compositions in treating disease or disorder, in particular for preventing, controlling or combating obesity. In another aspect the invention provides such compositions for the preparation of a medicament for use in treating any of the ailments or conditions herein described.

In at least one exemplary embodiment of the present disclosure, the composition comprises or consists of a mixture of at least two of the said plant extracts. In at least one other exemplary embodiment, the composition also includes one or more fat binding materials such as chitosan or a chitosan derivative. In at least one other exemplary embodiment, the composition also includes one or more amylase inhibiting compounds and/or one or more antioxidants such as vitamins A, C, or E.

The plant extracts are usefully obtained from dried or freeze dried plant components. The extract may be of the leaves, roots and/or stem of the plants. The extract may be dried powder or entirely aqueous-derived such extract, e.g. obtained by boiling the plant components in water, or derived from a mixture containing water and, for example, ethanol. A mixture of water and 50% by volume of ethanol is suitable and preferred. The extracts are also preferably ion exchange unbound and resin scavenged prior to use and formulation with chitosan or chitosan derivative. It is possible, but less preferred to use extracts derived from the solvent dichloromethane.

Preferably, in the case of plants of the *Cissus* family, the plant components used in making the extract are the leaves, roots and/or stem. Preferably the extracts are aqueous and can be produced by a simple, conventional extraction technique, although it is more preferable that the plant components be dried before addition of water and boiling the mixture.

Such compositions can be formulated for human consumption and demonstrate one or more of the following other properties:
(1) Reduces the amount of fat absorbed by the body,
(2) Increases the amount of fat in feces,
(3) Increases fecal bulk,
(4) Reduces carbohydrate breakdown in vitro,
(5) Reduces carbohydrate breakdown in vivo,
(6) Inhibits salivary amylase activity,
(7) Inhibits intestinal amylase activity,
(8) Decreases the acidity of the stomach,
(9) Increases the amount of cholesterol in feces,
(10) Reduces post-prandial blood glucose,
(11) Inhibits intestinal lipase activity,
(12) Reduces the body mass index (weight) of subjects.

Example 1

Preparation of the mixture: Plants of the *Cissus* family, *Vernonia* family, and *Brillantasia* family:
Plant component used: Leaves, stems and roots
Preparation method: The leaves, stems and roots are dried at 45° C. for 72 hours. The dried samples are transferred into 2 times their weight of water and boiled for 1 hour. The mixture is left to stand for 2 hours at room temperature before straining to remove any residue. The resultant supernatant is stored at 4° C. until required.

*Brillantasia* sp.
Plant component used: Leaves
Preparation method: The leaves are harvested from the plant and dried at 45° C. for 72 hours. The dried leaves are finely ground into a powder, then transferred into 2 times their weight of boiling water. This is left to stand for two hours at room temperature before straining to remove leaf residue. The resultant supernatant was stored at 4° C. until required.

*Cissus* sp. and *Vernonia* sp. Combination
Although all combinations of extracts of plants of the three families, namely *Cissus* sp., *Vernonia* sp. and *Brillantasia* sp. had an enhancing effect, optimal activity was obtained using the following mixture of two aqueous plant extracts:

*Cissus* sp. extract 50-90%, more preferably 60-80% most preferably 70% (v/v), *Vernonia* sp. 10-50% more preferably 20-40% most preferably 30% (v/v). This is a preferred specific mixture of *Cissus* sp. and *Vernonia* sp.

Application and Dose
The mixture can be taken orally at a concentration of 0.1 to 10 ml, preferably 0.1 to 5 ml, more preferably 0.2 to 2 ml, most preferably 0.5 ml per kilogram body weight with or before a meal.

Example 2

Plant materials: *Vernonia glabra* (root) and *Cissus quadrangularis* (leaf and stem) were harvested from the Western and Centre Provinces of Cameroon respectively. The plant material was washed and dried for three days in an oven at 55° C. The dried material was then ground, sieved and stored until required. Chitosan based formulations were made as show in Table 1 (increasing concentration of plant extract and decreasing chitosan content).

TABLE 1

Composition of different chitosan based formulations

| Constituents (mg) | $CF_0$ | $CF_1$ | $CF_2$ | $CF_3$ | $CF_4$ |
|---|---|---|---|---|---|
| Chitosan | 250 | 200 | 170 | 150 | 100 |
| Vitamin C | 60 | 60 | 60 | 60 | 60 |
| Plant powder | 0 | 50 | 80 | 100 | 150 |

In Vitro Binding Studies
The ability of various chitosan combinations to bind triacylglycerol was carried out as described below. A specific weight (1-4 g) of chitosan or the chitosan combination was weighed out and incubated with shaking at 37° C. for 2 hours with 6 g soya oil and 10 ml hydrochloric acid (10 mmol/L). The acid was then neutralized and 10 ml phosphate buffered saline (pH 7.4) added. Incubation with shaking was continued for a further 3 hours at 37° C., after which the tubes were centrifuged at 2500 rpm for 30 min. Unadsorbed fat floated on the surface, was aspirated and weighed. This gave the amount of triacylglycerol not bound to the chitosan combination.

Subjects
Seventy four overweight (BMI 25-30 $kg/m^2$) women (19-32 years) were recruited to take part in the study. They gave their written consent after details of the trial had been verbally explained to them and could drop out of the study at anytime they wanted without having to give reason. Ethics approval was obtained from the Joint University/Ministry of Health Ethics committee, Cameroon.

Subjects were randomly allocated one of four treatments in a double blinded study. The results are for fifty nine subjects who completed the study. The control group received maize flour, while the other groups received either chitosan, chitosan plus *Vernonia glabra* (16% w/w) or chitosan plus *Cissus quadrangularis* (16% w/w). All subjects were required to consume 2 g of the control or test material twice daily before their main meals.

Diet
The subjects were asked not to change their food habits and to maintain their normal diets as much as possible. They kept individual food diaries which were used to analyze food intake using food tables.

Fecal Collections and Analysis
Feces were collected for four consecutive days every other week, in special glass containers and brought daily to the laboratory for storage. All subjects were instructed to bring in their samples as soon as was possible. The feces was weighed and the pH measured. An aliquot (2 g) of the feces was used for the determination of total lipid using the method described by Folch, et al. (1957). The dry matter weight was determined using a homogenate of the total feces collected (three days drying at 55° C.).

Fecal ash was determined after 48 hours incineration at 500° C. Fecal calcium and magnesium was determined using the modified methods described by SIGMA company. In these methods, the ash was dissolved in nitric acid solution (3N) and the calcium and magnesium assayed spectrophotometrically using arsenazo dye III and calmagite respectively. Total nitrogen was determined by the Kjeldahl procedure. Statistical significance was determined using paired Student's t-test.

Results
In Vitro Lipid Binding
The in-vitro lipid binding of the different chitosan formulations is shown Table 2. The highest lipid binding was obtained with the formulation $CF_1$ for each of the two plant powders containing 16% (w/w) of the plant. *Cissus quadrangularis* however bound more (P<0.001) lipid than *Vernonia glabra* (P<0.01). Other combinations containing *Cissus quadrangularis* enhanced the binding of soya oil. The binding was however not as high as for the $CF_1$ combination containing 16% (w/w) plant powder.

TABLE 2

The effect of Chitosan formulations on in-vitro lipid (Soja oil) binding (g/g of Chitosan formulation). mean ± S.D

| Plant Powder | Chitosan formulations | | | | |
|---|---|---|---|---|---|
| | $CF_0$ | $CF_1$ | $CF_2$ | $CF_3$ | $CF_4$ |
| V. glabra | 13.70 ± 2.04 | 22.04 ± 2.79** | 17.81 ± 4.09 | 12.49 ± 4.78 | 10.44 ± 4.9 |
| C. quadrangularis | 13.70 ± 2.04 | 27.80 ± 0.47** | 22.60 ± 6.52** | 18.03 ± 1.17* | 14.89 ± 2.05 |

*P < 0.01
**P < 0.001

Food Intake

The average energy and nutrient intake of subjects is given in Table 3. This is similar to the intake of that age group of women in Cameroon.

TABLE 3

The mean of total energy, lipid, carbohydrate, protein, calcium, magnesium and fiber of subject dietary intake

| | mean ± SD |
|---|---|
| ENERGY (Kcal/day) | 2346.48 ± 535.55 |
| LIPID (g/day) | 92.93 ± 28.00 |
| CARBOHYDRATE (g/day) | 367.51 ± 64.54 |
| PROTEIN (g/day) | 83.50 ± 15.15 |
| FIBER (g/day) | 22.41 ± 5.58 |
| CALCIUM (mg/day) | 421.78 ± 243.98 |
| MAGNESIUM (mg/day) | 134.58 ± 45.86 |

Fecal Composition

During the first week of the trial, only the formulation containing *Vernonia glabra* (16%, w/w) significantly (p<0.05) increased fecal wet weight as well as fecal dry weight (Table 4). On maintaining intake for a longer period (more than one month), chitosan (CFO) significantly reduced the fecal moisture content and increased (p<0.05) fecal pH, while the formulation containing *Vernonia glabra* significantly (p<0.05) reduced fecal pH.

Table 4 demonstrates the ability of chitosan to reduce pH, which is possibly as a result of the formation of glucosamine in the intestine. At this low pH, there is a modification of bile acid metabolism.

The reduction of fecal pH and moisture content noticed is reversed by the inclusion of *Cissus quadrangularis*.

This study has shown a negative correlation between the fecal moisture and the fecal pH (r=−0.477) and even between fecal moisture and the root square of fecal pH[(pH)$^{1/2}$] (r=−0.465), P<0.001. So the reduction of fecal moisture can be explained by the increase of the fecal pH.

The reduction of fecal moisture is also dependent on the ash content since fecal moisture is negatively correlated to the fecal ash content (mg/g of FDW) (r=−0.301), P<0.01 (Table 5).

TABLE 5

Correlation between different fecal components

| Variable | r(N = 80) | Probability(P) |
|---|---|---|
| moisture, pH | −0.477 | P < 0.001 |
| moisture, (pH)$^{1/2}$ | −0.465 | P < 0.001 |
| moisture, ash | −0.301 | P < 0.01 |
| ash, pH | +0.248 | P < 0.05 |
| calcium, pH | −0.221 | P < 0.05 |
| moisture, calcium | +0.030 | N.S |
| ash, calcium | −0.069 | N.S |
| pH, Nitrogen | 0.232 | P < 0.05 |
| ash, Nitrogen | +0.009 | N.S |
| moisture, Nitrogen | +0.011 | N.S |

Chitosan as well as the chitosan formulation containing *Cissus quadrangularis* significantly (p<0.05) increased the fecal calcium concentration after one month of treatment (Table 6). The formulation containing *Vernonia glabra* however brought about a decrease in the concentration of fecal calcium. It is likely that the increased concentration of calcium in feces is as a result of contribution from the chitosan. There however seems to be a factor in the formulation containing *Vernonia glabra* that causes an increased retention of calcium.

Unlike calcium, magnesium concentrations in the feces was not altered by any of the formulations (Table 6).

Fermentation of chitosan in the large intestine produces glucosamine which can be absorbed (application in arthritis) by the body. Glucosamine can also bring about an increase in gut pH which favors the absorption of nitrogenous compounds (negative correlation between fecal pH and total fecal nitrogen, r=−0.232; p<0.05). The formulation containing *Vernonia glabra* however significantly (p<0.05) increased the amount of nitrogen present in the feces (Table 6). This increase is still significant even when the amounts contributed by the presence of chitosan is taken into consideration. On the other hand, fecal nitrogen is significantly (p<0.05) reduced by the chitosan formulation containing *Cissus quadrangularis*.

*Vernonia glabra* therefore seems to play a role in inhibiting the absorption of nitrogenous compounds which will otherwise be favored by an increase in pH.

Chitosan as well as chitosan based formulations significantly (p<0.01) increased the total amount of lipid in the feces (Table 7). This is as a result of the ability of chitosan to bind lipids in the gut. (It will however be interesting to investigate what happens to the mixture of lipids, chitosan and glucosamine in the large intestine).

These results support the hypothesis that phytochemical substances in some plants can improve the ability of chitosan to bind lipids and contribute to weight loss without negatively altering the calcium and magnesium status of the subject.

The results show that the chitosan only formulations increase fecal pH and cause constipation while $CF_1.V$ decreased the fecal pH. These results suggest that the long term intake of chitosan might cause colon cancer while the use of $CF_1.V$ can benefit overweight and obese patients.

TABLE 4

The effect of chitosan formulations on fecal wet and dry weight, pH and moisture

| Measures | Control (n = 20) | | Chitosan (n = 21) | | Chitosan + V.g (n = 18) | | Chitosan + C.q (n = 21) | |
|---|---|---|---|---|---|---|---|---|
| | $D_0$ | $D_{>30}$ | $D_0$ | $D_{>30}$ | $D_0$ | $D_{>30}$ | $D_0$ | $D_{>30}$ |
| Fecal wet weight (g/d) | 165.4 ± 26.4[a] | 187.8 ± 41.5[a] | 185.7 ± 24.6[a] | 180.2 ± 16.7[a] | 178.5 ± 39.0[a] | 264.2 ± 33.0[b] | 188.1 ± 28.6[a] | 187.8 ± 82[a] |
| Fecal dry weight (g/d) | 26.3 ± 5.3[a] | 28.5 ± 9.8[a] | 29.0 ± 5.3[a] | 28.9 ± 9.7[a] | 28.2 ± 8.2[a] | 36.0 ± 9.4[b] | 28.2 ± 7.7[a] | 27.2 ± 9.4[a] |
| Fecal moisture % | 79.8 ± 4.9[a] | 80.1 ± 5.2[a] | 78.6 ± 5.9[a] | 72.6 ± 6.7[b] | 79.1 ± 4.0[a] | 81.0 ± 4.5[a] | 78.9 ± 3.8[a] | 74.9 ± 6.1[ab] |
| Fecal pH | 6.9 ± 0.6[a] | 6.8 ± 0.8[ac] | 6.9 ± 0.4[a] | 7.4 ± 0.3[b] | 6.8 ± 0.2[a] | 6.5 ± 0.3[c] | 6.9 ± 0.5[a] | 7.0 ± 0.3[a] |

Values are 4-days means ± S.E.
Values without a common superscript are significantly different (P < 0.05)

TABLE 6

The effect of chitosan formulations on fecal ash, calcium and magnesium and nitrogen

| Measures | | Control (n = 20) | | Chitosan (n = 21) | | Chitosan + V.g (n = 18) | | Chitosan + C.q (n = 21) | |
|---|---|---|---|---|---|---|---|---|---|
| | | $D_0$ | $D_{>30}$ | $D_0$ | $D_{>30}$ | $D_0$ | $D_{>30}$ | $D_0$ | $D_{>30}$ |
| Fecal ash | g/d | 2.5 ± 1.1[a] | 3.0 ± 0.9[a] | 2.7 ± 1.4[a] | 5.2 ± 3.7[b] | 3.0 ± 1.3[a] | 3.7 ± 1.8[ab] | 2.8 ± 1.8[a] | 5.4 ± 2.5[b] |
| Calcium | mg/d | 100.1 ± 23.7[a] | 117.6 ± 12.3[a] | 104.4 ± 10.8[a] | 180.3 ± 85.5[b] | 88.4 ± 34.2[ac] | 65.1 ± 15.2[c] | 109.4 ± 15.3[a] | 130.1 ± 14.3[b] |
| Magnesium | mg/d | 83.5 ± 21.3[a] | 76.5 ± 16.9[a] | 89.6 ± 17.6[a] | 100.5 ± 32.5[a] | 82.3 ± 11.4[a] | 89.4 ± 14.2[a] | 91.1 ± 21.1[a] | 92.5 ± 12.9[a] |
| Nitrogen ($N_2$) | mg/d | 354.5 ± 128.5[a] | 384.3 ± 194.3[a] | 391.7 ± 133.6[a] | 421.7 ± 355.0[a] | 379.9 ± 170.9[a] | 1039.5 ± 540[b] | 380.6 ± 164.5[a] | 371.1 ± 196.4[a] |
| $N_2$-Chitosan$N_2$ | mg/d | 354.5 ± 128.5[a] | 384.3 ± 194.3[a] | 391.7 ± 133.6[a] | 312.9 ± 355.0[a] | 379.9 ± 170.9[a] | 930.7 ± 540.1[b] | 380.6 ± 164.5[a] | 371.1 ± 196.4[c] |

Values are 4-days means ± S.E.
Statistical significance is by comparison within a specific measured parameter. Values without a common superscript are significantly different (P < 0.05)

TABLE 7

The effect of chitosan formulations on total lipid excretion

| Measures | Control (n = 20) | | Chitosan (n = 21) | | Chitosan + V.g (n = 18) | | Chitosan + C.q (n = 21) | |
|---|---|---|---|---|---|---|---|---|
| | $D_0$ | $D_{>30}$ | $D_0$ | $D_{>30}$ | $D_0$ | $D_{>30}$ | $D_0$ | $D_{>30}$ |
| Total lipid (mg/g)[a] g/d | 73 ± 15[a] 8.4 ± 3.7[a] | 87 ± 15[a] 10.0 ± 4.0[a] | 83 ± 16[a] 9.6 ± 4.1[a] | 163 ± 18[b] 29.4 ± 14.2[b] | 86 ± 19[a] 9.9 ± 4.5[a] | 183 ± 12[b] 48.3 ± 9.2[b] | 88 ± 16[a] 10.2 ± 3.9[a] | 161 ± 6[b] 30.3 ± 13.2[b] |

Values are 4-days means ± S.E. Values without a common superscript are significantly different (P < 0.01)

Example 3

The Effect of Chitosan Based Formulations on Body Composition in Overweight Women Chitosan and chitosan based formulations containing *Cissus quadrangularis* and *Vernonia glabra* were administered to sixteen overweight (BMI>25 kg/m2) women on an energy restricted diet supplemented with vitamins and minerals over a period of eight months. There was a significant reduction in the BMI of subjects given chitosan as well as the chitosan based formulations (4 grams per day) containing the plant extracts (16%, w/w), with the most significant reduction observed in subjects who received the chitosan based formulation containing *Cissus quadrangularis*. A significant reduction in the circulating levels of cholesterol and total triglycerides was observed in all the chitosan based groups.

Materials and Methods

The following combinations were used for the study:
Group 1. Maize flour-Control group
Group 2. Chitosan plus vitamin C
Group 3. Chitosan plus vitamin C plus *Vernonia glabra*
Group 4. Chitosan plus vitamin C plus *Cissus quadrangularis*

Subjects

Thirty two overweight (BMI>25 kg/m²) women (24-36 years) were recruited for the study. They gave their written consent after details of the trial had been verbally explained to them. They could drop out of the trial at any time without need to explain their action. The results reported are for twenty subjects who completed the study. Subjects randomly allocated one of the four treatments above in a double blind study. All subjects were required to consume 2 g of the control or test material twice daily before their main meals.

Diet

The subjects were given a number of possible diets they could follow, which provided a total daily energy intake of 1500 kcal.

Body Mass Index (BMI) and Body Fat Content

The BMI of subjects was measured using an electronic scale and a meter rule attached to the wall. The percentage body fat was determined by using bioelectrical impedance measurements.

Blood Collection and Sampling

Venous blood (20 ml) was collected from the forearm of subjects, and serum prepared from it was stored in 1 ml vials at −70° C. until required. The concentration of total cholesterol and triglycerides were determined using Sigma kits.

Results

TABLE 8

Body Mass Index (kg/m$^2$). Values are means ± sem.

| | $D_0$ | $D_7$ | $D_{15}$ | $D_{30}$ | $D_{60}$ | $D_{90}$ | $D_{120}$ | $D_{150}$ | $D_{180}$ | $D_{210}$ |
|---|---|---|---|---|---|---|---|---|---|---|
| Control | 30.61 ± 2.03 | 30.61 ± 2.03 | 29.41 ± 2.42 | 29.21 ± 1.68 | 29.03 ± 1.76 | 29.03 ± 2.34 | 30.04 ± 1.67 | 29.87 ± .98 | 29.22 ± 2.10 | 28.69 ± 3.01 |
| Chitosan | 28.66 ± 1.78 | 28.60 ± 1.78 | 27.31 ± 2.02 | 26.02 ± 2.01 | 26.03 ± 1.67 | 25.34 ± 1.67 | 27.87 ± 1.87 | 28.02 ± 1.67 | 26.21 ± 2.02 | 26.04 ± 1.53 |
| Chitosan + Vernonia glabra | 29.92 ± 2.17 | 29.83 ± 2.18 | 28.33 ± 1.67 | 26.18 ± 1.78 | 25.87 ± 1.23* | 25.34 ± 1.56* | 25.02 ± 1.78* | 24.98 ± 1.82* | 25.38 ± 1.56* | 24.88 ± 1.67* |
| Chitosan + Cissus quadrangularis | 28.43 ± 1.53 | 28.62 ± 1.33 | 28.04 ± 1.89 | 26.44 ± 0.98 | 24.64 ± 1.22** | 23.40 ± 2.68** | 23.55 ± 2.67** | 25.60 ± 3.56 | 24.36 ± 1.78** | 24.31 ± 1.50* |

*$p \leq 0.05$;
**$p \leq 0.01$

Conclusions

Subjects on a daily average energy intake of approximately 1500 kcal did not show any significant change in BMI. Subjects on the formulations containing *Vernonia glabra* as well as *Cissus quadrangularis* had reduced BMIs after being on the formulation for 60 days.

TABLE 9

Body fat content (%)

| | $D_0$ | $D_7$ | $D_{15}$ | $D_{30}$ | $D_{60}$ | $D_{90}$ | $D_{120}$ | $D_{150}$ | $D_{180}$ | $D_{210}$ |
|---|---|---|---|---|---|---|---|---|---|---|
| Control | 39 ± 9 | 41 ± 12 (37 ± 8) | 39 ± 14 (35 ± 4) | 37 ± 12 (33 ± 3) | 39 ± 6 (32 ± 2) | 37 ± 5 (31 ± 3) | 38 ± 8 | 36 ± 6 | 38 ± 6 | 36 ± 6 |
| Chitosan | 37 ± 10 | 38 ± 8 (36 ± 8) | 38 ± 6 (33 ± 2) | 35 ± 9 (31 ± 2) | 34 ± 7 (31 ± 2) | 34 ± 6 (29 ± 2) | 32 ± 3 | 35 ± 8 | 33 ± 6 | 33 ± 5 |
| Chitosan + Vernonia glabra | 36 ± 9 | 37 ± 10 (36 ± 6) | 36 ± 12 (32 ± 3) | 34 ± 8 (30 ± 2) | 31 ± 9 (27 ± 2) | 29 ± 10 (25 ± 3) | 29 ± 8 (24 ± 3) | 28 ± 8* | 28 ± 8* | 28 ± 9 |
| Chitosan + Cissus quadrangularis | 37 ± 8 | 37 ± 8 (35 ± 4) | 36 ± 9 (32 ± 2) | 33 ± 8 (29 ± 3) | 29 ± 8 (25 ± 3) | 24 ± 9** (22 ± 2) | 24 ± 6** (21 ± 2) | 24 ± 7** | 23 ± 4** | 24 ± 5** |

*$p \leq 0.05$;
**$p \leq 0.01$ (The figures in brackets represent values for subjects who were on a daily energy intake of 800 kcal rather than 1500 kcal.)

Conclusion

There is a significant decrease in total body fat in the groups treated with the chitosan formulations in subjects maintained on a diet of 1500 kcal per day. In subjects maintained on an 800 kcal per day diet, a decrease in body fat was observed in all groups.

TABLE 10

| | Total blood cholesterol (g/L) | | | | |
|---|---|---|---|---|---|
| | Day 0 | Day 7 | Day 15 | Day 30 | Day 60 |
| Control | 1.70 ± 0.12 | 1.50 ± 0.09 | 1.54 ± 0.18 | 1.65 ± 0.15 | 1.58 ± 0.11 |
| Chitosan | 1.60 ± 0.06 | 1.44 ± 0.10 | 0.73 ± 0.06** | 0.92 ± 0.05** | 0.84 ± 0.12** |
| Chitosan + Vernonia glabra | 2.07 ± 0.11 | 1.78 ± 0.10 | 1.42 ± 0.08 | 1.37 ± 0.11 | 1.23 ± 0.30* |
| Chitosan + Cissus quadrangularis | 1.94 ± 0.14 | 1.19 ± 0.18 | 0.85 ± 0.09** | 0.81 ± 0.09** | 1.01 ± 0.11** |

*$p \leq 0.05$;
**$p \leq 0.01$
Significant differences are determined by comparing to the control for each time point.

Conclusion

Chitosan and the chitosan formulation containing *Cissus quadrangularis* were the most effective in lowering blood cholesterol levels for any given time point.

Considering the composition of the formulations containing the plant extracts, it is obvious that there is a component in *Vernonia glabra* that inhibits the reduction of blood cholesterol levels by chitosan. On the other hand, a component or components present in *Cissus quadrangularis* may potentate this reduction.

TABLE 11

| | Total blood triglycerides (g/L) | | | | |
|---|---|---|---|---|---|
| | Day 0 | Day 7 | Day 15 | Day 30 | Day 60 |
| Control | 1.84 ± 0.08 | 1.83 ± 0.08 | 1.76 ± 0.10 | 1.89 ± 0.09 | 1.76 ± 0.18 |
| Chitosan | 1.26 ± 0.13 | 1.18 ± 0.05 | 0.65 ± 0.14** | 0.83 ± 0.11* | 0.74 ± 0.10** |
| Chitosan + Vernonia glabra | 1.87 ± 0.31 | 1.19 ± 0.08* | 0.82 ± 0.09** | 0.73 ± 0.06** | 0.68 ± 0.08** |
| Chitosan + Cissus quadrangularis | 1.84 ± 0.32 | 1.49 ± 0.27 | 0.62 ± 0.14** | 0.84 ± 0.07** | 0.70 ± 0.10** |

*$p \leq 0.05$;
**$p \leq 0.01$
Significant differences are determined by comparing to the control for each time point.

Conclusion

Chitosan and chitosan formulations significantly decreased the circulating concentrations of triglycerides. This is as a result of their ability to bind triglycerides in vitro as well as in vivo. The presence of plant extracts did not seem to have a potentiating effect on the ability of chitosan to bind triglycerides.

Example 4

The effect of *Cissus quadrangularis* and *Vernonia glabra* combination on blood lipid levels.

The mixture used in this part of the work had the following composition:

| | |
|---|---|
| Chitosan | 61.8% |
| Vitamin C | 19.0% |
| Vernonia glabra powder | 5.7% |
| Cissus quadrangularis powder | 13.5% |

This mixture had a superior lipid binding capacity in vitro compared to other chitosan formulations containing either *Vernonia glabra* or *Cissus quadrangularis*.

In Vitro Lipid Binding Capacity of Mixture
32.6 grams oleic acid per gram of mixture.
Effect of Mixture on BMI in overweight adults (BMI>25)
Body Mass Index ($kg/m^2$)
Values are means±sem.

TABLE 12

| | $D_0$ | $D_7$ | $D_{15}$ | $D_{30}$ | $D_{60}$ | $D_{90}$ | $D_{120}$ | $D_{150}$ | $D_{180}$ | $D_{210}$ |
|---|---|---|---|---|---|---|---|---|---|---|
| Control | 30.61 ± 2.03 | 31.61 ± 2.03 | 29.41 ± 2.42 | 29.21 ± 1.68 | 29.03 ± 1.76 | 29.03 ± 2.34 | 30.04 ± 1.67 | 29.87 ± 1.98 | 29.22 ± 2.10 | 28.69 ± 3.01 |
| Chitosan | 28.66 ± 1.78 | 28.60 ± 1.78 | 27.31 ± 2.02 | 27.02 ± 2.01 | 26.03 ± 1.67 | 28.04 ± 1.67 | 27.87 ± 1.87 | 28.02 ± 1.67 | 26.21 ± 2.02 | 26.04 ± 1.53* |

TABLE 12-continued

|  | $D_0$ | $D_7$ | $D_{15}$ | $D_{30}$ | $D_{60}$ | $D_{90}$ | $D_{120}$ | $D_{150}$ | $D_{180}$ | $D_{210}$ |
|---|---|---|---|---|---|---|---|---|---|---|
| Chitosan + Vernonia glabra | 29.92 ± 2.17 | 29.83 ± 2.18 | 23.33 ± 1.67 | 26.18 ± 1.78 | 25.87 ± 1.23* | 25.34 ± 1.56* | 25.02 ± 1.78* | 24.98 ± 1.82* | 25.38 ± 1.56* | 24.88 ± 1.67* |
| Chitosan + Cissus quadrangularis | 28.43 ± 1.53 | 28.62 ± 1.33 | 28.04 ± 1.89 | 26.44 ± 0.98 | 24.64 ± 1.22** | 23.40 ± 2.68** | 23.55 ± 2.67** | 25.60 ± 3.56 | 24.36 ± 1.78* | 24.31 ± 1.50* |
| Chitosan + Cissus/Vernonia mixture | 28.71 ± 2.17 | 26.83 ± 1.38 | 25.40 ± 1.43 | 23.48 ± 1.28** | 23.47 ± 1.22** | 24.06 ± 1.33** | 23.02 ± 0.78** | 23.98 ± 1.82* | | |

*$p \leq 0.05$;
**$p \leq 0.01$

The chitosan formulation containing a mixture of *Cissus quadrangularis* and *Vernonia glabra* significantly reduced the BMI of overweight females faster than formulations containing either *Cissus quadrangularis* or *Vernonia glabra*. This synergistic effect is possibly as a result of a reduction in the available glucose substrate for use as a fuel (α-amylase inhibition by *Vernonia glabra*). Fat preferentially used as fuel.

The preferred specific mixture within the scope of the invention, has application because of its effects upon different physiological processes. Examples of preferred applications include the following:

1) Use in the management of obesity, overweight, weight maintenance, slowing down the addition of weight, reduction of bounce back during weight loss and complications resulting from obesity.

This includes conditions such as hyperlipidemia, hypercholesteremia and, inability to move freely.

2) Uses in the management of diabetes and complications resulting from diabetes. This includes hyperglycemia, ketonuria and diabetic coma.

3) Use in controlling gastric acidosis.

4) Use in the relief of constipation.

The above physiological processes are apparently brought about by action of the mixture on one or more of the following factors:

Reduction of fat absorbed by the body; Increases in the amount of fat in feces increase of fecal bulk;

Reduction of carbohydrate breakdown in vivo;

Decrease in acidity of the stomach;

Increase in the amount of cholesterol in the feces;

Reduction of post-prandial blood glucose; and/or

Reduction of Body mass index (BMI) and weight.

Inhibition of Salivary and Pancreatic Amylase Activity

Human salivary amylase (Sigma A0521) and porcine pancreatic amylase (Sigma A3176) were used as starting material. The substrate used was starch and the formation of maltose was used to quantify and measure the activity of the amylase. One unit of activity of the mixture reduced the activity of salivary amylase by 50%, and the activity of pancreatic amylase by 65%.

Decrease of Acidity of the Stomach

Laboratory animals were fed diets containing the mixture (0.5 ml/kg body weight) after an overnight fast.

The content of their stomachs had a higher pH than control animals.

Humans who ingested the mixture produced feces with a lower pH than control humans who had not ingested the mixture.

Inhibition of Pancreatic Lipase Activity

Pancreatic lipase (Sigma L9780) was used as used as starting material.

One unit of the mixture is the quantity that will reduce the activity that will reduce the activity of 0.48 units of lipase by 50%. (One unit of lipase will liberate 1.0 μl of 2-monoglyceride from 1,2-diglyceride per minute at 37° C., pH 8.1).

While the apparatus and method have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A method of improving blood glucose or blood cholesterol levels of a mammal in need thereof, the method comprising
administering a composition containing an effective amount of *Cissus quadrangularis* and one or more plants selected from one or more of the plant genuses *Brillantaisia* and *Vernonia* to a mammal, whereby the administering of the composition to the mammal is effective in improving blood glucose levels or blood cholesterol levels in the mammal.

2. The method of claim 1, wherein the one or more plants selected is *Vernonia glabra*.

3. The method of claim 1, wherein the one or more plants selected is *Brillantaisia* sp.

4. The method of claim 1, wherein the one or more plants selected are *Vernonia glabra* and *Brillantaisia* sp.

5. A method of reducing blood glucose or blood cholesterol levels in a mammal, the method comprising
administering an effective amount of *Cissus quadrangularis* and one or more plants selected from *Vernonia glabra* and *Brillantaisia* sp. to a mammal.

6. The method of claim 5 wherein the effective amount of *Cissus quadrangularis* plant genus and the one or more plants selected from *Vernonia glabra* and *Brillantasia* sp. reduces blood glucose or blood cholesterol levels in the mammal when administered thereto the mammal.

* * * * *